United States Patent [19]

Mayer et al.

[11] Patent Number: 4,500,358

[45] Date of Patent: Feb. 19, 1985

[54] FOAM CAPSULES

[75] Inventors: Jean P. Mayer, Colmar, France; Fritz Wittwer, Lupsingen, Switzerland

[73] Assignee: Warner-Lambert Company, Morris Plains, N.J.

[21] Appl. No.: 484,723

[22] Filed: Apr. 13, 1983

Related U.S. Application Data

[62] Division of Ser. No. 438,147, Oct. 29, 1982, abandoned.

[51] Int. Cl.$^3$ .................... C08L 89/00; A01N 25/34; B28B 1/38
[52] U.S. Cl. .................................. 106/122; 106/127; 106/128; 106/129; 106/135; 106/138; 206/0.5; 264/50; 264/301; 264/305; 424/15
[58] Field of Search ................. 428/402.22; 206/0.5; 427/213.35; 424/15; 106/135, 122, 128, 129; 264/50, 301, 305

[56] References Cited

U.S. PATENT DOCUMENTS

| | | | |
|---|---|---|---|
| 3,317,433 | 5/1967 | Eichel | 106/135 |
| 4,026,986 | 5/1977 | Christen et al. | 264/301 |
| 4,138,013 | 2/1979 | Okajima | 106/128 |
| 4,331,547 | 5/1982 | Stotts et al. | 106/129 |

*Primary Examiner*—Theodore Morris
*Attorney, Agent, or Firm*—Alan H. Spencer; Stephen Raines

[57] ABSTRACT

Foam capsules with telescopically engaged body and cap portions, also known as hard shell capsules, having a special wall structure, obtained by a microdispersion of a gas in a gelatin solution.

The capsule body and cap portions are formed by dip-molding the film-forming mixture obtained by a microdispersion of the gas in a gelatin solution; optionally with the inclusion of a plasticizer and/or coloring agent, and/or flavoring agent, and/or foam stabilizer, and/or gelatin extender.

By a suitable choice of the gas proportion in the capsule wall and its micronization level, it is possible, within certain limits, to control the capsule wall disintegration speed and its opacity. In addition, inclusion of gas bubbles into the capsule wall lowers the gelatin content for a foam capsule and provides energy saving during the process due to a faster drying of the wall, thereby providing lower cost prices for the production of pharmaceutically acceptable capsules.

32 Claims, No Drawings

FOAM CAPSULES

This is a division of application Ser. No. 438,147 filed Oct. 29, 1982 now abandoned.

SUMMARY

The present invention relates to a foam capsule. More particularly, the invention relates to pharmaceutically acceptable capsules having capsule body and cap portions, formed by dipmolding, using a film-forming mixture obtained by a microdispersion of a suitable gas in a gelatin solution;

As used herein, the term "gelatin" means gelatin and derivatives thereof.

As used herein, the term "gelatin foam" means a homogeneous mixture obtained by microdispersion of a gas in a gelatin solution.

The term "capsules" means hard shell capsules having telescopically engaged body and cap portions obtained by a dipmolding technique (see U.S. Pat. No. 3,173,840.)

The term "foam capsules" means such capsules, obtained by dipmolding into gelatin foams, the wall of which being formed by a homogeneous microdispersion of gas in dry gelatin.

As is known, capsules are a preferred form of administration for medicaments and similar products. However, in many cases, the disintegration speed of the gelatin capsules can vary considerably depending on the composition of the contents. For example, the disintegration of capsules containing a lipophilic medicament is delayed because of the lipophilic properties of the content. The rapid release of the medicament is thereby impaired which can have a detrimental effect on its bioavailability. In order to avoid these disadvantages, attempts have been made to ensure a rapid release of the capsule contents by means of a suitable form of the capsule walls, for example by providing them with holes or other apertures, as described in U.S. Pat. No. 3,620,759. Such capsules have, however, the disadvantage that, in the case of pulverulent contents, premature release of the contents takes place, during storage or transport. In order to avoid this undesirable, premature release of the capsules' contents, capsules of this type, having holes or other apertures, have been provided completely or partially with a coating of a water-soluble material, as described in U.S. Pat. No. 3,823,816. Although the undesirable, premature release of the capsules' contents can be largely avoided in this manner, the production of such capsule is difficult and expensive.

The objective of this invention was therefore to modify the capsule wall of gelatin capsules provided for medicinal and other purposes in such a manner that a control, particularly an acceleration, of the capsule disintegration can be achieved in a simple manner.

On the other hand, many additives used in pharmaceutical materials are now being critically examined. For example, titanium dioxide, commonly used as an opacifier in hard shell gelatin capsules, is under examination as to whether or not it is pharmaceutically acceptable.

A new capsule type, the wall of which would be opaque without addition of titanium dioxide or other similar chemicals and which could therefore contain only natural and biodegradable products, would have important advantages over conventional hard shell gelatin capsules.

It has been found in the present invention that it is possible to obtain white opaque film-forming mixtures by simple inclusion, followed by micronization, of suitable gases such as air, oxygen, nitrogen, carbon dioxide, argon, etc. into natural transparent gelatin solutions. The opacity and white color shade of the foam capsules obtained by dipmolding into such film-forming mixtures, is a function of the included gas quantity and of its micronization level.

It has also been found in the present invention that the stability of the foam increased in the following order or microdispersion of gases: carbon dioxide, oxygen, air, nitrogen and argon. However, economic considerations favor the use of air and nitrogen.

It has also been found that the particular structure of the wall of such foam capsules, assures, with regard to conventional hard shell gelatin capsules with a same wall thickness, a notable increase of the disintegration speed. This disintegration time can be varied by modifying both gas content and thickness of the wall. Increasing the gas content and/or decreasing the wall thickness, the disintegration time is reduced. Decreasing the gas content and/or increasing the wall thickness, the disintegration time is increased.

As a result of these discoveries, it was possible to achieve the objectives of the present invention and to provide a hard shell gelatin capsule, the wall of which is opaque without additives such as titanium dioxide, that decomposes at a particularly higher speed which can be controlled and which is suitable for medicinal purposes. This foam capsule is characterized in that the material forming the capsule wall is a foam obtained by microdispersion of a suitable gas in gelatin, optionally with the inclusion of a plasticizer and/or a coloring agent, and/or a flavoring agent, and/or a foam stabilizer, and/or a gelatin extender.

The gelatin foams, suitable to obtain foam capsules according to the present invention, are made from aqueous solutions of gelatin comprising between 10 to 50% by weight of gelatin, better in the range of 15 to 35% and best in the range of 21 to 28%. Different grades of pure gelatins or mixtures thereof can be used at pH values between 3.0 to 10.0, with better results in the range of pH 5.0 to 9.0.

The foam may be produced according to any of a number of common methods, wherein air, or a gas such as nitrogen, oxygen, argon, carbon dioxide or another suitable gas, or a mixture thereof, is mixed with the gelatin solution and micronized. The most suitable foaming devices are based on a mechanical action, such as obtained for example with a high-speed blender, or a baker's "whip" in which a wire whisk is both rotated and travels in a circular path, or with a centrifugal emulsifying device in which a rotor, rotating at high speed, forces the gas/gelatin mixture through a perforated stator where the bubbles are micronized. These devices can be used for batch foam production or most preferably in line, in systems where the foam flows continuously through a dish, where dipmolding is performed and is recirculated through a foaming reservoir wherein the gas/gelatin mixture is continuously micronized and where regulation of the optimal gas/water/gelatin content takes place. In-line foaming can be done in an open reservoir fitted with a gas supply and, for example, with a centrifugal emulsifier, in which case the diameter of the micronized gas bubbles is in a considerable measure controlled by the rotation speed of the rotor and the dimensions of the perforations of the stator and the gap between rotor and stator. Foaming can also be done in a closed chamber such as in a continuous pressure beater, commonly used in the food industry for aerated desserts or marshmallow confection. In the latter case, the foam is obtained by simultaneous injection of a controlled quantity of gas and gelatin solution into a mixing head formed by a rotor and a stator, both being fitted with a high number of teeth to accomplish micronization. The gas/gelatin ratio in the foam is controlled by the corresponding injection rates. The micronization level of the gas bubbles is, in a considerable measure, controlled by the number of teeth, the chamber configuration and the contact time of the foam in the mixing head.

Other suitable foam generation systems may be used such as aerosol generation, ultrasonic emulsifying, injecting gas into gelatin solution through micropipes, sintered glass or sintered metal, or passing of the gas/gelatin solution mixture through tubes packed with polyamide fibers or steel wool (as described in Netherlands Patent Application No. 7.609.307).

It is recommended to equip all the above devices with a heating system in order to avoid premature gelling of the foam.

Suitable foams for obtaining foam capsules by dip-molding according to the present invention are characterized by a gas content between 8 to 70% vol/vol of the gelatin solution better between 13 to 31%; a density between 0.3 to 1.1 g/cm3, better between 0.7 to 0.95; a viscosity between 200 and 2,000 centipoises, better between 400 to 900 centipoises; and, for obtaining a desired opacity, by a diameter of the dispersed gas bubbles between 0.001 microns and 150 microns, better between 0.01 microns and 70 microns, and best between 0.001 to 50 microns.

For capsule production, suitable metal mold pins are dipped in the conventional way into the gelatin foam and the wet film thus formed on the pins upon lifting from the foam is dried gradually to obtain the desired foam capsule parts. The wall thickness of capsules produced by dip-molding depends on the viscosity of the dipping solution. If a thin-walled capsule is desired, more water and/or less air are used in order to lower the viscosity, whereas if a thick-walled capsule is desired, less water and/or more air are added in order to increase the viscosity.

The wall thickness of the capsule is also dependent on the temperature of the dipping mixture. Depending upon the desired wall thickness and on the foam composition, the foam in the dipping dish is kept at a temperature between 30° to 65° C., better between 40° and 50° C. A condition for obtaining the foam capsule according to the present invention, is that the foam is sufficiently stable and durable, so that the uniformly dispersed gas bubbles are maintained while the foam is transferred from the foaming reservoir to the dipping dish.

A constant foam quality regulation is assured by simultaneous in-line viscosity and density measurements and subsequent addition of water and/or air and/or fresh gelatin solution.

In some cases, particularly when more diluted gelatin solutions are used, foam stabilizing agents may be added at varying concentrations. In general amounts of about 0.01 to 5% and preferably at 0.05 to 0.5% based upon the weight of gelatin have been found effective. Suitable illustrative foam stabilizing agents include, for example:

viscosity increasing agents such as alginic acid and salts thereof, xanthan, cellulose derivatives such as carboxymethylcellulose, hydroxypropycellulose, hydroxypropylmethylcellulose, microcrystalline cellulose, and the like;

vegetable gums such as carrageenates, pectin, agar and the like;

proteins such as albumin, hydrolyzed animal proteins and the like;

esters such as sucrose esters, fatty acid esters and ethoxylates thereof, particularly polyglycerol and sorbitol derivatives thereof; glycerides and derivatives thereof such as succinyl monoglycerides; acetic-,lactic-,citric-, or acetylated tartaric acid esters of monoglycerides; glycosides, and derivatives thereof, such as glycosides; lanolin and its derivatives and the like;

non-ionic surfactants such as fatty acid alkyolamides or ethoxylates thereof; amine oxides and particularly those containing long chain substituents such a N,N-dimethyldodecylamine, and substituted and unsubstituted long chain alcohols, such as lauryl alcohol, sorbitol monooleate and the like;

anionic surfactants such as alkylarylsulphonates, particularly sodium dodecylbenzenesulfonic acid, and alcoholsulphates, particularly sodium lauryl sulphate, ethersulphates and the like;

metal salts such as aluminum, calcium, potassium, and iron salts, and the like; and combinations of the above, particularly mixtures of egg albumin and microcrystalline cellulose or mixtures of non-ionic and anionic surfactants such as, for example, sodium lauryl sulphate and sorbitol monooleate or sodium lauryl sulphate and coconut fatty acid diethanolamide.

It must be noted, of course, that among the above-mentioned stabilizers, only approved foam stabilizers may be used for the production of foam capsules for food or pharmaceutical uses.

For manufacturing hard shell foam capsules according to the present invention, the utilization of pharmaceutical goods coloring agents, flavoring agents and plasticizers leads to optimal product qualities without destroying or substantially altering their valuable physical properties.

Pharmaceutically acceptable coloring agents such as azo-dyes, as iron oxides and hydroxides, natural dyes etc. are optionally used. In general acceptable concentrations of between about 0.001 to 10%, better between 0.001 to 5% based upon weight of gelatin have been found effective.

Flavoring agents accepted for pharmaceutical and food use are usually prepared by or derived from synthetic flavor oils and/or oils derived from plants, leaves, flowers, fruits, etc. as well as combinations thereof. Representative flavor oils include peppermint oil, cinnamon oil, spearmint oil, etc. Furthermore, natural or synthetic fruit flavors such as oils including lime, grape, orange, lemon, grapefruit and fruit essence including apple, pineapple, cherry, strawberry, etc. can be used.

The above flavoring agents are generally used at a concentration of about 0.01% to about 3% by weight on dry gelatin or derivatives thereof, better at about 0.2 to about 1.5%, and best at about 1.1%.

Plasticizers, particularly those of pharmaceutical grade, such as polyethylene glycol or preferably low molecular weight organic plasticizers, like glycerol, soribitol, dioctyl-sodium sulfosuccinate, triethyl citrate, tributyl citrate, 1,2-propylenglycol, mono-, di-and triacetates of glycerol etc. may be utilized at various concentrations of between about 0.2 to 15% better between 0.2 to 5% based upon the weight of the gelatin.

In addition it has been found that the foam capsules of the present invention can be produced with various grades of gelatin combined with extenders of between about 2 to 40% content, by weight, better between about 5 to 20%, such as sunflower proteins, soybean proteins, cotton seed proteins, peanut proteins, rape seed proteins and the like and better defatted qualities thereof. For manufacturing capsules with such gelatin extenders, and combinations thereof, the same kind of coloring agents, plasticizers, foam stabilizers and flavoring agents as described above, are suitable.

The foam capsules according to the present invention can be made, if desired with one or more locking features.

In the same manner as conventional hard shell gelatin capsules, foam capsules show optimal properties when the wall moisture content is between about 12 to 16%. In spite of the gas inclusion, the wall elasticity of foam capsules is similar to that of conventional hard shell gelatin capsules. An important advantage of the foam capsule is that it is considerably cheaper in manufacture than conventional hard shell gelatin capsules since a smaller amount of gelatin is required. For example, gelatin savings of between 40 to 50% can be reached without substantially altering the mechanical properties of foam capsules. In addition, since the particular structure of the wall of foam capsules provides a considerably increased exchange surface, an appreciable energy saving can be obtained during the manufacturing process because the wet half shells dry more easily and more rapidly on the mold bars than conventional hard gelatin capsule shells.

As mentioned above, the foam capsules have opaque walls, which effect is exclusively due to the homogeneous gas dispersion in the wall material and thus avoids the use of opacifying agents such as titanium dioxide or the like.

As described above, the possibility to obtain with foam capsules, within certain limits, controlled disintegration times and particularly shorter disintegration times than with conventional hard shell capsules, makes them suitable for a wide range of uses.

For example, capsules with moderate gas ratios in the wall, as obtained by dipping into gelatin foams having gas contents of between approximately 8 to 28% vol/vol, are useful for classical oral administration of medicaments. This means that they can be ingested without particular risk of premature opening in the mouth or in the esophagus. Their advantages over conventional hard shell gelatin capsules are a faster disintegration in the stomach, thereby maintaining an improved bioavailability of their contents, and less local irritations of the gastric mucous membrane may be obtained.

On the other hand, foam capsules with higher gas ratios in the wall are not adapted for classical oral administrations since the disintegration is so fast that a premature content release occurs in the mouth or in the esophagus. This particularity makes them especially suitable as chewing-capsules, or as capsules for sublingual administration, or in all cases where a fast absorption of the medicament by the mucous membrane of the mouth is desirable, as for nitroglycerine and certain steroid hormones, and particularly for those which are unstable under acidic conditions and are destroyed in the stomach.

In some cases, at low gas ratios in the wall and with thicker walls, the disintegration time of foam capsules is comparable with that of conventional hard shell gelatin capsules. A longer disintegration time is also obtainable with foam capsules. In this particular case the main advantage of foam capsules is the opacity of the wall without addition of opacifying agents.

An interesting effect of the micronization of gas bobbles in the wall of foam capsules is to provide a special configuration to the outer surface of the capsule wall (juxtaposed microbubbles) which confers to the foam capsules, when using only current approved natural and synthetic dyestuffs for pharmaceuticals, special and more brilliant color shades, like opalescent or pearly, which cannot be obtained for conventional hard shell gelatin capsules with the same dyestuffs.

Foam capsules may also be useful in other fields than pharmaceutical purposes, particularly in those cases where single dosage forms with a fast disintegration would be ideal such as:

food packaging, as for powdered instant coffee or spices;
candy manufacturing;
fertilization of ornamental plants and/or indoor plants;
packing of sensitive seeds in combination with protective agents and/or fertilizers; and
packing of single dyestuffs (or mixtures of various dyes) doses, at precise weight for quick preparation of dyestuff solutions and the like.

The present invention is illustrated by following examples:

EXAMPLE 1

A natural transparent aqueous solution of gelatin, at a concentration of 24% weight/weight, with an initial viscosity of 300 centipoise is poured into a foaming reservoir fitted with a water jacket, a centrifugal emulsifying device and an air introduction pipe.

During a first foaming step, air is introduced into the solution and micronized by the emulsifier, rotating at full speed (2,800 rpm), until an air content of 23% volume/volume, and a satisfactory micronization of the air bubbles are reached. The white opaque foam obtained has a temperature of 48° C. (water jacket at 45° C.), a viscosity of 800 centipoise and a density of 0.8 g/cm3.

In a second step, an exit valve or faucet from the foaming reservoir is opened and the foam flows by gravity towards the dipping dish wherein it is distributed through a longitudinal slit. The foam overflow is collected and reintroduced with a peristaltic pump into the foaming reservoir where it is recirculated through the emulsifier. The foam quality regulation is assured, over several hours, by simultaneous in-line viscosity and density measurements and subsequent addition of water and/or air and/or fresh gelatin solution.

For the formation of capsule halves by the dip-molding technique, previously lubricated metallic cap and body mold pins are dipped into the gelatin foam which flows through the dipping dish and are withdrawn and lifted slowly in conventional fashion to provide even distribution of the foam film layer over the effective area of each mold pin. The coated pins are then kept stationary for a sufficient period to gellify the film layer on the pin. The capsule halves thus formed are dried by blowing with air at about 30% relative humidity and at about 30° C., and are removed from the pins, trimmed and joined together with the other halves of the capsule to provide the finished foam capsule ready for filling.

To confirm that the obtained white opaque, slightly opalescent, foam capsules obtained have the described properties, the capsules are filled with lactose and subjected to a standard disintegration test in an Erweka apparatus according to the method described in the European Phamacopeia, 2nd. Edition, 1980, Part 1, V.5.1.1.

TABLE 1

Compared disintegration times in seconds between foam capsules and conventional gelatin capsules

| Capsule type | Wall thickness ($.10^{-3}$ in.) | Mean opening time (on 6 capsules) | Mean disintegration time (on 6 capsules) |
|---|---|---|---|
| Foam capsule | 5 | 30 | 81 |
| Conventional capsule | 4 | 82 | 195 |

As table 1 shows, in spite of a 25% thicker wall, the disintegration of the tested foam capsules is 58% faster than for conventional capsules.

TABLE 2

Weight evaluation

| Mean weight foam capsules | 52 mg |
|---|---|
| Normal reference capsule | 78 mg |

As shown in Table 2, manufacturing of the described foam capsules allows a gelatin saving of 33%.

TABLE 3

Compared drying speeds at 30° C. and 30% RH (measured is the required time for to obtain capsule walls with 20% moisture content)

| Capsule type | Time (min.) |
|---|---|
| Foam Capsule | 24 |
| Normal ref. capsule | 38 |

Table 3 shows that the drying of the described foam capsules is 37% faster than for conventional capsules.

EXAMPLE 2

The production of the foam capsules was the same as in Example 1, but the influence of different air content values and wall thicknesses on disintegration time was checked.

TABLE 4

Disintegration time as a function of air content and wall thickness (on every 6 capsules)

| Sample reference capsule | % of air v/v in the foam before drying | Wall thickness ($.10^{-3}$ inches) | Disintegration time (in sec.) |
|---|---|---|---|
| conventional standard | — | 4 | 195 |
| Foam 1 | 15% | 4 | 149 |
| Foam 2 | 15% | 5.5 | 173 |
| Foam 3 | 20% | 5.5 | 140 |
| Foam 4 | 23% | 5 | 81 |
| Foam 5 | 23% | 6 | 108 |
| Foam 6 | 26% | 6.5 | 96 |
| Foam 7 | 29% | 5.5 | 64 |

The above demonstrates that with a suitable choice of the air proportion in the capsule wall and of the wall thickness, it is possible, within certain limits to control the disintegration time.

EXAMPLE 3

The production of colored foam capsules was the same as in Example 1, but, before foam generation, the following dyes or pigments were mixed with the gelatin solution at a concentration of 0.5% based upon weight of dry gelatin.

Red : azorubine
Blue : patent blue
Yellow : tartrazine
Black : black iron oxide

The colored foam capsules were opaque, and had similar disintegration times, as the corresponding white opaque capsules described in Example 1 above. In addition, the colored foam capsules were characterized by new, more brilliant, opalescentlike, color shades than for conventional capsules.

EXAMPLE 4

The production of flavored capsules was the same as in example 1 but, before foam generation, peppermint oil as a flavoring agent was added at a concentration of 0.6% based upon the weight of dry gelatin.

EXAMPLE 5

Example 1 was repeated by adding 2% of glycerol, based on dry gelatin weight, in the gelatin solution. The additive did not affect the ability to generate a suitable foam, and the disintegration time of the obtained capsules remained similar.

EXAMPLE 6

Example 1 was repeated by adding 0.2% sodium lauryl sulphate and 0.2% sorbitan monooleate, based on dry gelatin weight, in the gelatin solution. The additives did not affect the disintegration time of the obtained capsules, but increased notably the lifetime of the gelatin foam circulating in the dish.

EXAMPLE 7

Example 1 was repeated by replacing the air with nitrogen. This replacement did not affect the ability to generate a suitable foam, and the disintegration time of the obtained capsules remained similar.

While there have been described and illustrated several embodiments of the present invention, the scope and working range of the invention shall not be limited by the examples given above. The invention comprises as well various changes and modifications which will occur to those skilled in the art.

It is intended in the appended claims to cover all such changes and modifications as fall within the true spirit and scope of the present invention.

What is claimed is:

1. A method for the formation of capsule halves by the dipmolding technique and thereby for the production of a foam capsule with telescopically engageable body and cap halves of an unfilled foam capsule adopted to be filled, the joined halves of the capsule providing the finished foam capsule adopted for filling, which method comprises
   A. dissolving gelatin water to make an aqueous gelatin solution;
   B. mixing a gas into the aqueous gelatin solution to make a gas and aqueous gelatin solution;

C. micronizing the gas and aqueous gelatin solution to make a micronized gas and aqueous gelatin solution; and forming by the dipmolding technique telescopically engageable body and cap halves of unfilled foam capsules from the micronized gas and aqueous gelatin solution.

2. The method of claim 1 wherein in step A the gelatin solution is in a pH range of between about 3.0 to 10.0.

3. The method of claim 1 wherein in step A the gelatin in the aqueous gelatin solution is in a range of between about 10 to 50% by weight of gelatin.

4. The method of claim 1 wherein in step B the gas is air.

5. The method of claim 1 wherein in step B the gas is a gas selected from a group consisting of carbon dioxide, oxygen, air, nitrogen, argon or a mixture thereof.

6. The method of claim 1 wherein in step C the micronizing of the gas in an aqueous gelatin solution is accomplished mechanically by blender, a baker's whip, a centrifugal emulsifier or a continuous pressure beater.

7. The method of claim 1 wherein in step C the micronizing of the gas in an aqueous gelatin solution is accomplished by simultaneous injection of a controlled quantity of the gas and gelatin solution into a mixing head having a rotor and a stator, both of which having a number of teeth to micronize the gas.

8. The method of claim 1 wherein in step C the micronizing of the gas in an aqueous gelatin solution is accomplished by aerosol generation or ultrasonic emulsification.

9. The method of claim 1 wherein in step C the micronizing of the gas in an aqueous gelatin solution is accomplished by injecting gas through micropipes, sintered glass or sintered metal; or by passing the gas and aqueous gelatin solution through tubes packed with polyamide fiber or steel wool.

10. The method of claim 1 wherein in step C the micronizing of the gas and aqueous gelatin solution is accomplished within a heating system to avoid premature gelling of foam.

11. The method of claim 1 wherein in step C the micronized gas and aqueous gelatin solution has a gas content range between about 8 to 70% by volume, a density range between about 0.3 to 1.1 grams per cubic centimeter, a viscosity range between about 200 to 2,000 centipoises, and by air bubbles having a diameter range between about 1 and 150 microns.

12. The method of claim 1 wherein in step C the micronized gas and aqueous gelatin solution is maintained at a temperature range between about 30° to 65° centigrade.

13. The method of claim 1 wherein in any of steps A, B or C a pharmaceutically acceptable foam stabilizing agent is added having a concentration range of about 0.01 to 5.0% based upon the weight of the gelatin.

14. The method of claim 13 wherein the foam stabilizing agent is selected from a group of viscosity increasing agents consisting of alginic acid and salts thereof, xanthan, cellulose derivatives such as carboxymethyl cellulose, hydroxypropylcellulose, hydroxypropylmethylcellulose, microcrystalline cellulose, and mixtures thereof.

15. The method of claim 13 wherein the foam stabilizing agent is selected from a group of vegetable gums, consisting of carrageenates, pectin, agar, and mixtures thereof.

16. The method of claim 13 wherein the foam stabilizing agent is selected from a group of proteins consisting of albumin, hydrolyzed animal proteins and mixtures thereof.

17. The method of claim 13 wherein the foam stabilizing agent is selected from a group of non-ionic substances, consisting of fatty acids alkylolamides or ethoxylates thereof, amines and amine oxides with one to three long chain substituents of between 8 to 20 carbon atoms, particularly lauryl alcohol; and mixtures thereof.

18. The method of claim 13 wherein the foam stabilizing agent is selected from a group of esters consisting of sucrose esters; fatty acid esters and ethoxylates thereof, particularly polyglycerol and sorbitan derivatives thereof; glycerides and derivatives thereof consisting of succinyl monoglycerides; acetic-, lactic-, citric- or acetylated tartaric acid esters of monoglycerides, glycosides, ethoxylated glycosides; lanolin and its derivatives, and mixtures thereof.

19. The method of claim 13 wherein the foam stabilizing agent is selected from a group of anionic surfactants consisting of fatty alkylarylsulphonates, particularly sodium dodecylbenzenesulfonic and; alcoholsulphates, particularly sodium lauryl sulphate; and mixtures thereof.

20. The method of claim 13 wherein the foam stabilizing agent is selected from a group of metal salts consisting of aluminum, calcium, potassium iron salts and mixtures thereof.

21. The method of claim 13 wherein the foam stabilizing agent is selected from the following groups surfactants consisting of:

viscosity increasing agents consisting of alginic acid and salts thereof, xanathan, cellulose derivatives such as carboxymethyl cellulose, hydroxypropylcellulose, hydroxypropylmethylcellulose, microcrystalline cellulose, and mixtures thereof;

vegetable gums consisting of carrageenates, pectin, agar and mixtures thereof;

proteins consisting of albumin, hydrolyzed animal proteins and mixtures thereof;

esters consisting of sucrose esters, fatty acid esters and ethoxylates thereof, particularly polyglycerol and sorbitan derivatives thereof; glycerides and derivatives thereof consisting of succinyl monoglycerides; acetic-, lactic-, citric-, or acetylated tartaric acid esters of monoglycerides; glycosides, and derivatives thereof, consisting of glycosides; lanolin and its derivatives and mixtures thereof;

non-ionic surfactants consisting of fatty acid alkyolamides or ethoxylates thereof; amine oxides and particularly those containing long chain substituents such a N,N-dimethyldodecylamine, and sbustituted and unsubstituted long chain alcohols, consisting of lauryl alcohol, sorbitol monooleate and mixtures thereof;

anionic surfactants consisting of alkylarylsulphonates, particularly sodium dodecylbenzenesulfonic acid, and alcoholsulphates, particularly sodium lauryl sulphate, ethersulphates and mixtures thereof; and metal salts consisting of aluminum, calcium, potassium, and iron salts, and mixtures thereof.

22. The method of claim 14 wherein more than one foam stabilizing agent is selected from any of the groups in claims 14 to 21 and pharmaceutically acceptable combinations thereof.

23. The method of claim 1 wherein in any of steps A, B or C a pharmaceutically acceptable coloring agent is added having a concentration range of about 0.001 to 10.0% based upon the weight of the gelatin.

24. The method of claim 23 wherein the coloring agent is an azo-dye.

25. The method of claim 23 wherein the coloring agent is an iron oxide.

26. The method of claim 23 wherein the coloring agent is a natural dye.

27. The method of claim 1 wherein in any of steps A, B or C a pharmaceutically acceptable flavoring agent is added.

28. The method of claim 1 wherein in any of steps A, B or C a pharmaceutically acceptable plasticizer is added having a concentration range of about 0.2 to 15.0% based upon the weight of the gelatin.

29. The method of claim 28 wherein the plasticizer is polyethylene glycol.

30. The method of claim 28 wherein the plasticizer is selected from a group of low gram molecular weight organic plasticizers consisting of glycerol, sorbitol, di-octyl-sodium sulfosuccinate, triethyl citrate, tributyl citrate, 1,2-propylene glycol, mono-, di-and triacetates of glycerol.

31. The method of claim 1 wherein in any of steps A, B or C a gelatin extender is added having a cooncentration range of about 2 to 40% based upon the weight of the gelatin.

32. The method of claim 31 wherein the gelatin extender is a protein selected from a group consisting of sunflower proteins, soybean proteins, cotton seed proteins, peanut seed protein, rape seed proteins.

* * * * *